United States Patent [19]
Jones

[11] Patent Number: 5,820,372
[45] Date of Patent: Oct. 13, 1998

[54] DENTAL IMPRESSION TRAY

[75] Inventor: Joseph W. Jones, Forest Hills, N.Y.

[73] Assignee: Temrex Corp., Freeport, N.Y.

[21] Appl. No.: 801,578

[22] Filed: Feb. 14, 1997

[51] Int. Cl.⁶ ................................................ A61C 9/00
[52] U.S. Cl. ........................................................ 433/38
[58] Field of Search ............................... 433/37, 38, 41, 433/43, 71

[56] References Cited

U.S. PATENT DOCUMENTS

| | | |
|---|---|---|
| 3,468,029 | 9/1969 | Moore ........................................ 433/38 |
| 3,890,711 | 6/1975 | Burns ......................................... 433/41 |
| 4,449,927 | 5/1984 | Taylor et al. . | 
| 4,619,610 | 10/1986 | Pelerin . |
| 4,689,010 | 8/1987 | Wolfe . |
| 5,102,335 | 4/1992 | Getz .......................................... 433/38 |
| 5,636,985 | 6/1997 | Simmen et al. ...................... 433/38 X |

*Primary Examiner*—Nicholas D. Lucchesi
*Attorney, Agent, or Firm*—Hoffman, Wasson & Gitler

[57] ABSTRACT

A disposable bite tray received in a bite tray holder, having interconnected buccal and lingual support members, slidingly receiving the disposable bite tray, having a buccal plate member and a lingual plate member, that holds more material along the outer surface than the inner surface of a patient's teeth in an ergonomically friendly package.

12 Claims, 2 Drawing Sheets

DENTAL IMPRESSION TRAY

BACKGROUND OF THE INVENTION

1. Field of the Invention

This invention relates to dental instruments for taking impressions of teeth.

2. Description of the Prior Art

Dentists preparing crowns, inlays, bridges and the like routinely take impressions of the area targeted for a dental casting or fabrication with the use of dental impression trays. Since dental work must accommodate not only the surrounding teeth, but opposing teeth, impression trays have been developed is for conveying impressionable material into the mouth to accept the impressions of the upper and lower teeth. Once the material cures, the device and material is removed from the patient's mouth. The resultant mold is used to create a prostheses to fit into the target area of the mouth.

Often times, a patient requires extensive work which may span a gap where two or three teeth are missing. In this case, it is especially difficult to harmoniously mate the fabricated prostheses with the natural opposing teeth. In this case, it is helpful for a dentist to be able to use a impression tray that accommodates an extended impression of the area. Owing to the arched configuration of the palate and jaw, the impression tray must be able to bring into contact with the outer surface of the teeth more material than with the inner surface of the teeth. For economy, the impression tray should be able to receive disposable bite trays which receive the moldable material.

Another important aspect of the present dental tool which must not be overlooked is the relationship it has with the patient. A tool that causes great discomfort in the patient will either not be accepted or may not be allowed to seat properly in order to take a good impression of the teeth. The need exists for a dental impression tray which can convey more material to the outer surface of the teeth with a disposable bite tray that is ergonomically compatible or comfortable to the patient.

Several types of dental impression trays are described in the patent literature. Unfortunately, the apparatuses described do not provide for application for more material to the exterior surfaces of the teeth than the interior surfaces of the teeth in a comfortable disposable tray. For example, U.S. Pat. No. 4,449,927, issued May 22, 1984, to James C. Taylor et al. describes a dental instrument for simultaneously taking an impression and a bite occlusion. Referring to FIG. 2, the device includes a bite tray which is received in a bite tray holder. Although the device does provide for a disposable bite tray, the device provides for roughly equivalent amounts of moldable material on each side of the teeth of which the impression is being made.

U.S. Pat. No. 4,619,610, issued Oct. 28, 1986 to Joseph J. Pelerin, and U.S. Pat. No. 4,689,010, issued Aug. 25, 1987, to Herbert Wolfe, describe a dental impression tray in which a layer of wax or thermoplastic material is disposed. The device includes a integrally formed bite tray with support members on either side. An integrally-formed bite tray and bite tray holder does not provide the advantages of a holder with a removable, disposable tray.

Clearly, the above demonstrates a need for a dental impression tray including a removable, disposable bite tray which is received in a bite tray holder that provides more moldable material to the outer surfaces of the teeth and is patient friendly.

None of the above references, taken alone or in combination, are seen as teaching or suggesting the presently claimed dental impression tray.

SUMMARY OF THE INVENTION

The present invention overcomes the limitations of the above inventions by providing a disposable bite tray which is received in a bite tray holder that can hold excess material in the outer side of the teeth in an ergonomic package. The invention includes a bite tray holder having a buccal support member and a lingual support member connected thereto. A bite tray having a buccal plate member and a lingual plate member is slidingly received in the bite tray holder. Moldable material is deposited on the bite tray and maintained thereon by the bite tray holder. A handle is attached to the bite tray holder for easy insertion of the device into a patient's mouth. The bite tray holder is shaped in such a manner that it is comfortable when being used on a patient.

In consideration of the above, a first object of the invention is to provide a dental impression tray for receiving moldable material that may be used to take impressions of teeth.

A second object of the invention is to provide a dental impression tray that provides more moldable material to the exterior surfaces of the teeth than to the interior surfaces of the teeth.

A third object of the invention is to provide a dental impression tray which is ergonomically harmonious with a patient.

A fourth object of the invention is to provide a dental impression tray holder for receiving moldable material that may be used to take impressions of teeth.

A fifth object of the invention is to provide a dental impression tray holder that provides more moldable material to the exterior surfaces of the teeth, then the interior surfaces of the teeth.

A sixth object of the invention is to provide a dental impression tray holder which is ergonomically harmonious with a patient.

A seventh object of the invention is to provide improved elements and arrangements thereof in an apparatus for the purposes describes, which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features of the invention consistently throughout the attached drawings.

DETAILED DESCRIPTION OF THE PREFERRED EMBODIMENTS

Figure 1:
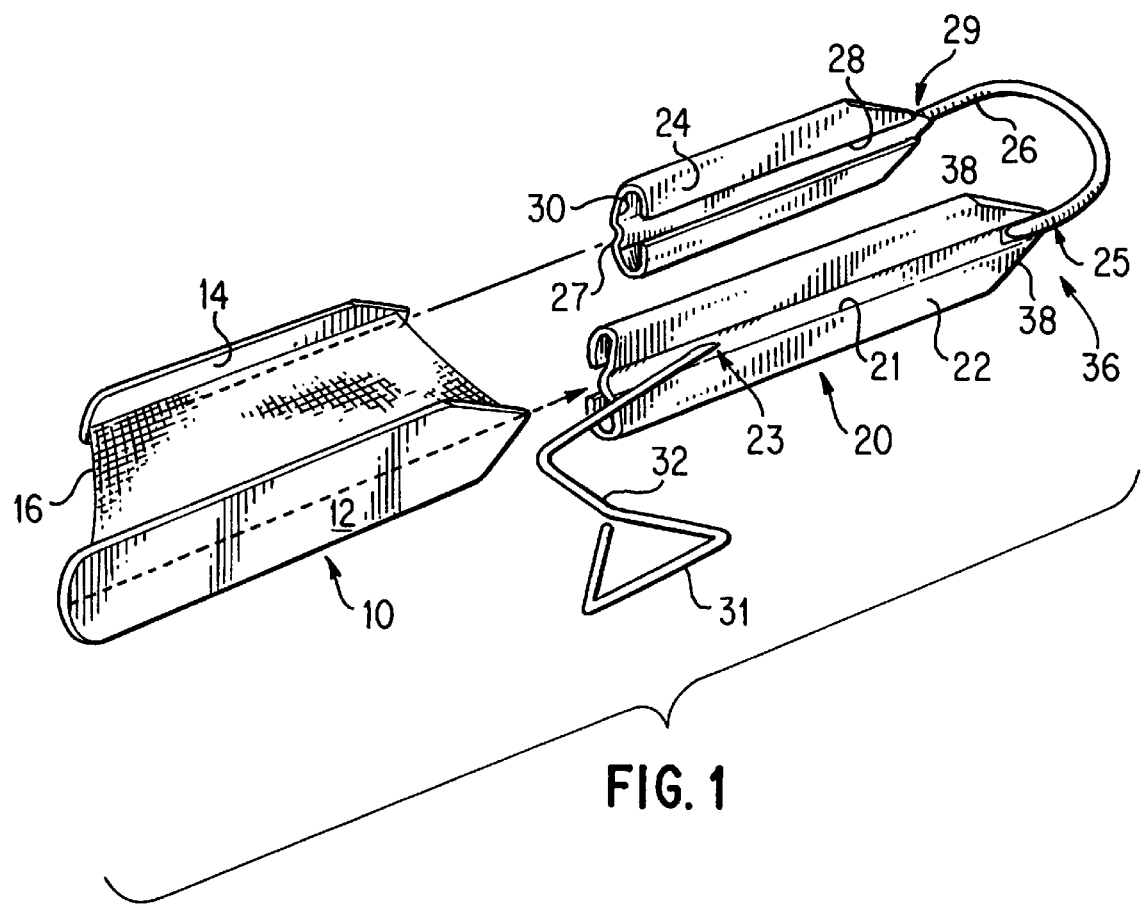
FIG. 1 is an prospective view of the invention.

Referring to FIG. 1, the present dental impression tray includes a removable bite tray 10 The bite tray 10 includes a buccal plate member 12 having a length and a lingual plate member 14 having a length. The plate members 12 and 14 are constructed from fairly rigid material, such as cardboard or other material commonly accepted in dental practice. In practice, the buccal plate member 12 and lingual plate member 14 have the same length. However, the invention does not exclude use of a buccal plate member 12 and lingual plate member 14 of differing lengths.

Figure 3:
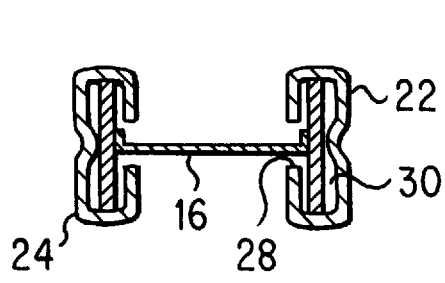
FIG. 3 is a front elevational view of the invention.

Referring also to FIG. 3, the bite plate 16 is interposed between plate members 12 and 14. The bite plate 16 is constructed from gauze or a like material and is fixed by any suitable manner.

The device also includes a bite tray holder 20. The bite tray holder includes a buccal support member 22 and a lingual support member 24 which are interconnected by a connecting member 26. Each support member 22 and 24 may be formed from an elongated flat plate with the edges rolled inward toward each other to define a longitudinal slot 28 and a sleeve 30. Each sleeve receives the appropriate plate member of the bite tray 10, the bite plate 16 being removably received within the slot 28. The bite tray holder 20 is provided with a handle 32 with which the dentist may insert the present device into a patient's mouth. The handle 32 may assume any shape that affords the user the greatest amount of dexterity with the present invention. Preferably, the handle 32 has at its distal end a round-, triangular- or diamond-shaped grip 31.

The buccal support member 22 also may have a longitudinal channel 21 that receives the inner end 23 of the handle 32 and the buccal end 25 of the connecting member 26. Similarly, the lingual support member 24 may have a longitudinal channel 27 that receives the lingual end 29 of connecting member 26. The channels 21 and 27 provide structural rigidity to the bite tray 20. The channels 21 and 27 also provide locally indented areas for positive location of the handle and connecting member ends for welding.

The buccal support member 22, lingual support member 24, buccal plate member 12 and lingual plate member 14 all may be substantially straight. The narrow, straight channel defined by the device accommodates a great number of differently shaped tooth and mouth configurations.

Figure 2:
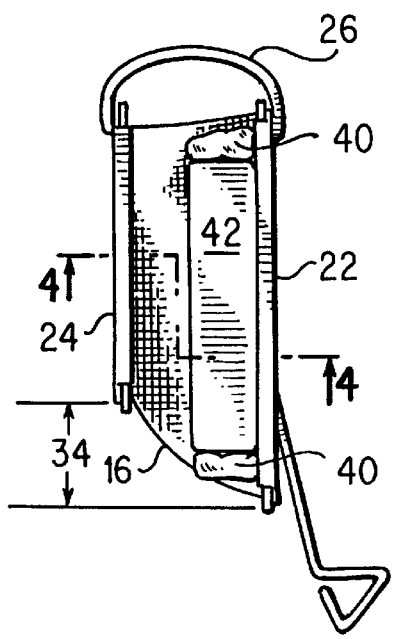
FIG. 2 is a plan view of the invention.

Referring to FIG. 2, the device provides a buccal support member 22 having a length that is greater than the length of the lingual support member 24. The difference between the length of the buccal support member 22 and the length of the lingual support member 24 defines a variance 34. Preferably, this variance 34 is approximately 0.5 inches. Ideally, the length of the lingual support member 24 should be approximately 1.25 inches, and the length of the buccal support member 22 should be approximately 1.75 inches.

Although the bite tray holder has support members of differing lengths, the bite tray 10 sliding received therein, in practice, does not assimilate this shape. Rather, the buccal plate member 12 and lingual plate member 14 have the same length. Alternatively, the present bite tray 10 may be dimensioned to compliment the present bite tray holder. Accordingly, the difference between the length of the buccal plate member 12 and the length of the lingual plate member 14 would define a second variance (not shown) substantially equivalent to the variance 34. This second variance, preferably, also would be approximately 0.5 inches.

Referring only to FIG. 1, the device provides for an ergonomically friendly device for use with a patient. The bite tray holder 20 has a back end 36 which is machined to more comfortably fit into a patient's mouth. The back end 36 of the bite tray holder 20 is tapered backwardly. Specifically, the back end of the bite tray support has a taper 38 such that the rear most portion of the bite tray support is quite smaller than the forward portion of the device.

Accordingly, where the lingual plate member 14 and buccal plate member 12 are coextensive with the lingual member 24 and the buccal member 22, the bite tray 10 may have a back end part of the original device, no longer interfere with or damage the roof or gums of a patient.

Figure 4:
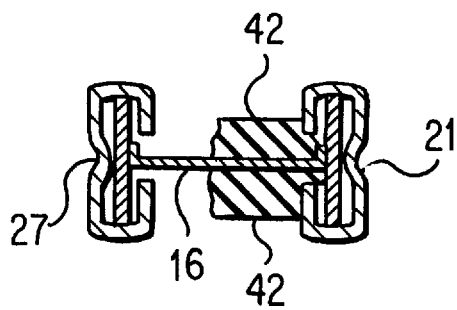
FIG. 4 is a cross-sectional detail view, taken on line 4—4 of FIG. 2, of the invention.

Referring to FIGS. 2 and 4, when in use, postdam wax 40 is placed on each side of the bite plate 16 at the anterior and posterior borders thereof. Postdam wax is a soft utility wax which functions generally to seal an area and is conventionally used in the dental art. A heavy rubber base material 42 is disposed between the two depositions of postdam wax 40. It should be understood that any type of moldable material commonly used in the dental industry may be used instead of the disclosed heavy rubber base material 42 disclosed.

Figure 5:
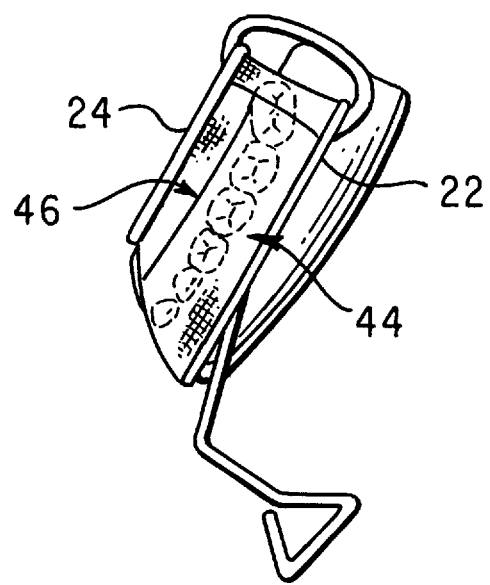
FIG. 5 is an environmental plan view of the invention placed within the mouth of a patient.

Referring to FIG. 5, the device is placed over a row of teeth. Due to the curvature of the jaw or palate shown, the outer surface 44 presented by the teeth is greater than that presented by the inner surface 46 of the teeth. For this reason, an extended buccal support member 22 and complimentary buccal plate member 12 accommodates a greater amount of moldable material than the relatively shorter lingual support member 24 and complimentary lingual plate member 14.

The present invention is not intended to be limited to the sole embodiments described above, but to encompass any and all embodiments within the scope of the following claims.

I claim:

1. A bite tray holder comprising:
   a buccal support member having an outwardly facing surface, having a front edge and a back edge longitudinally spaced from the front edge; and
   a lingual support member, having a front edge and a back edge longitudinally spaced from the front edge, connected to said buccal support member;
   wherein said buccal support member has a longitudinal channel formed in the outwardly facing surface.

2. A bite tray holder as recited in claim 1, wherein a variance is created by the length of said buccal support member being greater than the length of said lingual support member.

3. A bite tray holder as recited in claim 1, wherein said buccal support member has a taper such that its rear most portion is smaller than its forward portion; and
   said lingual support member has a taper such that its rear most portion is smaller than the forward portion.

4. A bite tray holder as recited in claim 1, further comprising:
   a removable bite tray, disposed on said bite tray holder, comprising:
   a buccal plate member having a length; and
   a lingual plate member, having a length, connected to said buccal plate member.

5. A bite tray holder as recited in claim 4, wherein said removable bite tray has a back end that is tapered backwardly.

6. A bite tray holder as recited in claim 4, wherein said length of said buccal plate member is greater than said length of said lingual plate member, a difference therebetween defining a second variance.

7. A bite tray holder as recited in claim 6, wherein said second variance is 0.5 inches.

8. A bite tray holder as recited in claim 1, further comprising a connecting member interposed between said buccal support member and said lingual support member.

9. A bite tray holder as recited in claim 1, further comprising a handle having an inner end that is received in said channel.

10. A bite tray holder as recited in claim 1, further comprising a connecting member having a buccal end received in said channel.

11. A bite tray holder as recited in claim 1, wherein said lingual support member has a longitudinal channel.

12. A bite tray holder as recited in claim 11, further comprising a connecting member having a lingual end received in said channel of said buccal support member.

* * * * *